United States Patent [19]
Arkans

[11] 4,308,870
[45] Jan. 5, 1982

[54] VITAL SIGNS MONITOR

[75] Inventor: Edward J. Arkans, Schaumburg, Ill.

[73] Assignee: The Kendall Company, Boston, Mass.

[21] Appl. No.: 156,246

[22] Filed: Jun. 4, 1980

[51] Int. Cl.³ ............................................. A61B 5/02
[52] U.S. Cl. .................................... 128/640; 128/671; 128/715; 128/721; 128/736; 338/38
[58] Field of Search ................................ 128/639–641, 128/644, 670, 671, 687–690, 736, 721–723, 774, 782, 775, 171; 73/777; 338/6, 36, 38

[56] References Cited
U.S. PATENT DOCUMENTS

| | | | |
|---|---|---|---|
| 2,486,625 | 11/1949 | Allen | 338/6 |
| 2,517,553 | 8/1950 | Fowler | 338/36 X |
| 3,268,845 | 8/1966 | Whitmore | 128/721 X |
| 3,290,521 | 12/1966 | Coleman et al. | 128/721 X |
| 3,307,547 | 3/1967 | Jones et al. | 128/171 |
| 3,483,861 | 12/1969 | Tiep | 128/721 |
| 4,047,144 | 9/1977 | Wong | 338/6 X |
| 4,055,839 | 10/1977 | Skeggs | 128/775 X |
| 4,079,731 | 3/1978 | Danby | 128/641 |
| 4,082,086 | 4/1978 | Page | 128/640 |

*Primary Examiner*—Lee S. Cohen
*Attorney, Agent, or Firm*—Powell L. Sprunger

[57] ABSTRACT

A vital signs monitor comprising, a plurality of pads having a front surface for contacting the chest of a patient, and containing equipment for monitoring a body function of the patient. The monitor has a device connected between a pair of pads for detecting expansion and contraction of the patient's chest.

13 Claims, 4 Drawing Figures

VITAL SIGNS MONITOR

BACKGROUND OF THE INVENTION

The present invention relates to monitoring devices, and more particularly to such devices for the human body.

Before the present invention, various equipment, such as ECG electrodes, temperature sensors, and microphones, have been utilized to separately monitor body functions of a patient. However, in certain cases, such as critically ill patients, it is desirable to continuously monitor a plurality of the body functions in order to alert the hospital staff in the event of an emergency resulting from a failing body function.

SUMMARY OF THE INVENTION

A principal feature of the invention is the provision of a monitor for the vital signs of a patient.

The monitor of the invention comprises a plurality of pads having a front surface for contacting the chest of a patient, and containing equipment for monitoring body functions of the patient. The monitor has means connected between a pair of pads for detecting movement of the patient's chest.

A feature of the invention is that the pads contain a plurality of ECG electrodes for monitoring the electrical activity of the heart.

Another feature of the invention is that at least one of the pads contains a microphone for detecting heart sounds.

Still another feature of the invention is that at least one of the pads contains a temperature sensor for detecting the body temperature of the patient.

Yet another feature of the invention is that the detecting means detects expansion and contraction of the patient's chest.

Thus, a feature of the invention is that the detecting means monitors the breathing rate of the patient.

Further features will become more fully apparent in the following description of the embodiments of this invention and from the appended claims.

DESCRIPTION OF THE PREFERRED EMBODIMENTS

Figure 1:
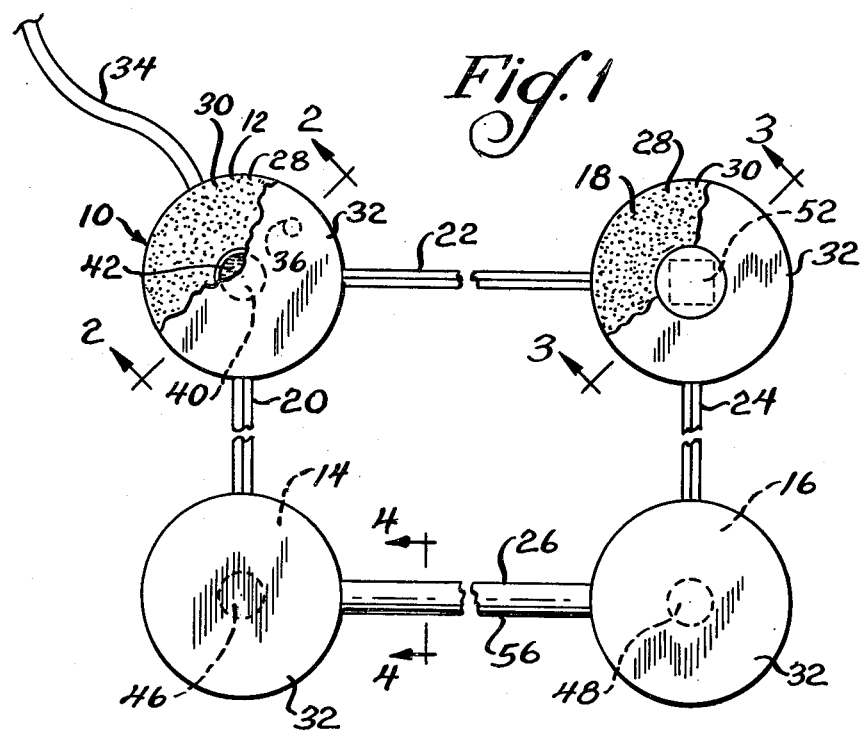
FIG. 1 is a fragmentary front plan view, partly broken away, of a vital signs monitor of the present invention.
Figure 2:
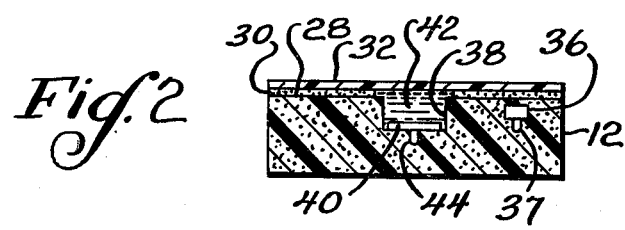
FIG. 2 is a sectional view taken substantially as indicated along the line 2—2 of FIG. 1.
Figure 3:
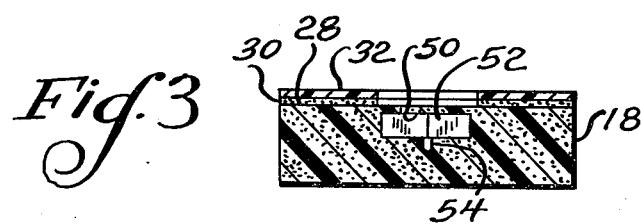
FIG. 3 is a sectional view taken substantially as indicated along the line 3—3 of FIG. 1.

Referring now to FIGS. 1-3, there is shown a vital signs monitor generally designated 10 having a plurality of pads 12, 14, 16, and 18 which may be constructed in cylindrical shape from a suitable flexible material, such as foam. The pads 12-18 are connected by leads 20, 22, and 24 and a detection device 26 such that the pads are arranged in a generally rectangular configuration. The pads 12-18 have a front surface 28 for contacting the chest of a patient, and adhesive 30 on the front surface 28 for attaching the pads to the chest. The adhesive 30 on each of the pads 12-18 is covered by a release sheet 32, such that the release sheets 32 may be removed to expose the adhesive 30 at the time of use. The monitor 10 has a cord 34 for connection to electrical monitoring equipment, as will be further discussed below.

With reference to FIGS. 1 and 2, the pad 12 has a temperature sensor 36, such as a thermistor, embedded in the pad 12 adjacent the front surface 28 of the pad. An electrical lead 37 extends from the temperature sensor 36 to the cable 34 for connection to suitable temperature monitoring equipment. The pad 12 also has a central recess 38 to receive an ECG electrode 40 at the bottom of the recess 38, with a suitable conductive gel 42 filling the recess 38 intermediate the electrode 40 and the front surface 28 of the pad 12. The electrode 40 may be made of a suitable metal as known to the art. The electrode 40 is connected to a lead 44 which extends to the cable 34. The pads 14 and 16 are similar to the pad 12, and contain suitable recesses of similar nature to receive ECG electrodes 46 and 48 and conductive gel in a manner as previously described. The electrode 46 is connected through leads 20 to the cable 34, and the electrode 48 is connected through the leads 22 and 24 to the cable 34. In turn, the cable 34 may be connected to suitable equipment for monitoring the signals from the ECG electrodes 40, 46, and 48.

With reference to FIGS. 1 and 3, the pad 18 has a cavity 50 to receive a sound detection device 52, such as a microphone or hydrophone, adjacent the front surface 28 of the pad 18. The microphone 52 is connected to one or more leads 54 which are connected by the leads 22 to the cable 34. The cable 34 may be connected to suitable monitoring equipment for the microphone 52.

In use, the release sheets 32 are removed from the pads 12-18 and the front surfaces 28 of the pads 12-18 are attached to the chest of a patient. The electrodes 40, 46, and 48 in combination with the ECG equipment are utilized to monitor the electrical activity of the heart. The temperature sensor 36 and associated equipment is utilized to monitor the skin temperature of the patient, while the sound detection device 52 and associated equipment is utilized to monitor the heart sounds of the patient.

Figure 4:
FIG. 4 is a sectional view taken substantially as indicated along the line 4—4 of FIG. 1.

With reference to FIGS. 1 and 4, the detection device 26 comprises a tube 56 of elastic material, such as rubber, which extends between the adjacent pads 14 and 16. A lumen 57 of the tube 56 is filled with a liquid conductive material 58, such as mercury. When the tube 56 between the pads 14 and 16 is stretched and the diameter of the tube 56 decreases, the electrical resistance of the conductive material 58 in the tube 56 increases. On the other hand, when the tube 56 between the pads 14 and 16 relaxes and the diameter of the tube 56 increases, the resistance of the conductive material 58 diminishes. The conductive material 58 is electrically connected through the leads 20, 22, and 24 to the cable 34 which in turn is connected to suitable equipment to measure the electrical resistance of the conductive material 58 in the tube 56. Thus, the monitoring equipment measures movement of the pads 14 and 16 relative to each other to detect stretching and relaxation of the tube 56 responsive to expansion and contraction of the patient's chest during breathing, i.e., the tube 56 stretches responsive to expansion of the chest since the pads 14 and 16 are attached at fixed locations on the patient's chest by the adhesive 30, while the tube 56 relaxes responsive to contraction of the chest. Accordingly, the tube 56, and conductive material 58 of the detection device 26 and associated equipment may be utilized to determine the breathing rate of the patient.

Thus in accordance with the present invention, the monitoring device permits simultaneous and continuous monitoring of the electrical activity of the heart, the skin temperature, heart sounds, and breathing rate of the patient.

The foregoing detailed description is given for clearness of understanding only, and no unnecessary limitations should be understood therefrom, as modifications will be obvious to those skilled in the art.

I claim:

1. A vital signs monitor, comprising:
   at least two pads having a front surface for contacting the chest of a patient, and means for connecting said pads together;
   means connected between said two pads for detecting movement of the chest; and
   means in said pads for monitoring a body function of the patient, with at least one of said pads containing an ECG electrode, and a conductive lead connected to said electrode.

2. The monitor of claim 1 wherein the pads comprise a foam material.

3. The monitor of claim 1 wherein the detecting means comprises an elastic tube extending between adjacent pads, said tube having a lumen filled with a liquid conducting material.

4. The monitor of claim 3 wherein the conducting material comprises mercury.

5. The monitor of claim 1 wherein the pads include adhesive on the front surface for attachment of the pads to the patient.

6. The monitor of claim 1 wherein the detecting means detects expansion and contraction of the patient's chest.

7. A vital signs monitor, comprising:
   at least two pads having a front surface for contacting the chest of a patient, and means for connecting said pads together;
   means connected between said two pads for detecting movement of the chest; and
   means in said pads for monitoring a body function of the patient, with at least one of said pads containing a sound detection device, and a conductive pad connected to the sound detection device.

8. The monitor of claim 7 wherein the detection device comprises a microphone.

9. A vital signs monitor, comprising:
   at least two pads having a front surface for contacting the chest of a patient, and means for connecting the pads together;
   means connected between said two pads for detecting movement of the chest; and
   means in said pads for monitoring a body function of the patient, with at least one of said pads containing a temperature sensor, and a conductive lead connected to said sensor.

10. A vital signs monitor, comprising:
    four pads having a front surface for contacting the chest of a patient;
    means connected between a pair of said pads for detecting movement of the chest; and
    means in said pads for monitoring a body function of the patient, with the monitor including means connecting the pads in a generally rectangular configuration.

11. The monitor of claim 10 wherein the connecting means for said pads comprises leads extending between adjacent pads and electrically connected to the monitoring means.

12. A vital signs monitor comprising, four pads including means for connecting the pads in a rectangular configuration, with three of said pads having ECG electrodes, at least one of said pads different from the pads with the electrodes having a sound detection device, at least one of said pads having a temperature sensor, and a plurality of conductive leads individually connected to said electrodes, sound detection device, and sensor.

13. The monitor of claim 12 including means connected between a pair of said pads for detecting expansion and contraction of the chest.

* * * * *